(12) United States Patent
Moorman et al.

(10) Patent No.: US 12,402,972 B2
(45) Date of Patent: Sep. 2, 2025

(54) CRANIAL ACCESS DEVICE

(71) Applicant: Monteris Medical Corporation, Minnetonka, MN (US)

(72) Inventors: James Patrick Moorman, Eden Prairie, MN (US); Walter John Dobrovolny, Saint Paul, MN (US); Jack Michael Mondry, Edina, MN (US); Mark Andrew Grant, Winnipeg (CA)

(73) Assignee: Monteris Medical Corporation, Minnetonka, MN (US)

( * ) Notice: Subject to any disclaimer, the term of this patent is extended or adjusted under 35 U.S.C. 154(b) by 526 days.

(21) Appl. No.: 17/661,241

(22) Filed: Apr. 28, 2022

(65) Prior Publication Data

US 2023/0346501 A1     Nov. 2, 2023

(51) Int. Cl.
*A61B 90/11*     (2016.01)
*A61B 90/10*     (2016.01)

(52) U.S. Cl.
CPC ......... *A61B 90/11* (2016.02); *A61B 2090/103* (2016.02)

(58) Field of Classification Search
CPC .............. A61B 90/11; A61B 2090/103; A61B 17/3468
See application file for complete search history.

(56) References Cited

U.S. PATENT DOCUMENTS

| | | | |
|---|---|---|---|
| 4,600,013 A | 7/1986 | Landy et al. | |
| 5,116,345 A * | 5/1992 | Jewell | A61B 90/11 606/130 |
| 7,604,658 B2 | 10/2009 | Wilson et al. | |
| 8,961,535 B2 | 2/2015 | Burg et al. | |
| 9,445,793 B2 | 9/2016 | Solar et al. | |
| 9,510,909 B2 | 12/2016 | Grant et al. | |
| 9,980,745 B2 | 5/2018 | Burg et al. | |
| 10,327,830 B2 | 6/2019 | Grant et al. | |
| 10,543,016 B2 | 1/2020 | Cantor et al. | |
| 10,743,927 B1 * | 8/2020 | Osa | A61B 17/863 |
| 10,765,450 B2 * | 9/2020 | Mark | A61B 90/50 |
| 10,786,325 B1 * | 9/2020 | Osa | A61B 90/10 |

(Continued)

FOREIGN PATENT DOCUMENTS

| | | | |
|---|---|---|---|
| CN | 104921800 B | | 3/2018 |
| EP | 0195455 B1 * | | 2/1990 |

(Continued)

OTHER PUBLICATIONS

International Search Report and Written Opinion dated Jan. 25, 2023, issued in Application No. PCT/US2022/071984 (10 pages).

*Primary Examiner* — Tan-Uyen T Ho
*Assistant Examiner* — Khoa Tan Le
(74) *Attorney, Agent, or Firm* — Fox Rothschild, LLP

(57) ABSTRACT

The disclosure provides a cranial access device that reduces or eliminates artifacts during imaging. The cranial access device includes a cranial bolt and a drive adapter. The cranial bolt includes a distal threaded portion, a proximal drive portion comprising a plurality of protrusions that form an external drive geometry, and a central passageway configured for receiving a neurosurgical tool. The drive adapter includes a distal end configured to receive and interface with the external drive geometry of the proximal drive portion, and a proximal end configured to receive a driver tool.

18 Claims, 9 Drawing Sheets

(56) References Cited

U.S. PATENT DOCUMENTS

| | | | |
|---|---|---|---|
| 2004/0242993 A1* | 12/2004 | Tajima | G01R 33/285 |
| | | | 600/417 |
| 2005/0251144 A1* | 11/2005 | Wilson | A61B 17/3403 |
| | | | 606/108 |
| 2008/0147128 A1* | 6/2008 | Fritzinger | A61B 17/862 |
| | | | 606/104 |
| 2013/0211202 A1 | 8/2013 | Perez-Cruet et al. | |
| 2020/0323492 A1 | 10/2020 | Bobo, Sr. et al. | |
| 2021/0128196 A1 | 5/2021 | Carroll et al. | |

FOREIGN PATENT DOCUMENTS

| | | |
|---|---|---|
| WO | 2013112477 A1 | 8/2013 |
| WO | 2021011795 A1 | 1/2021 |

* cited by examiner

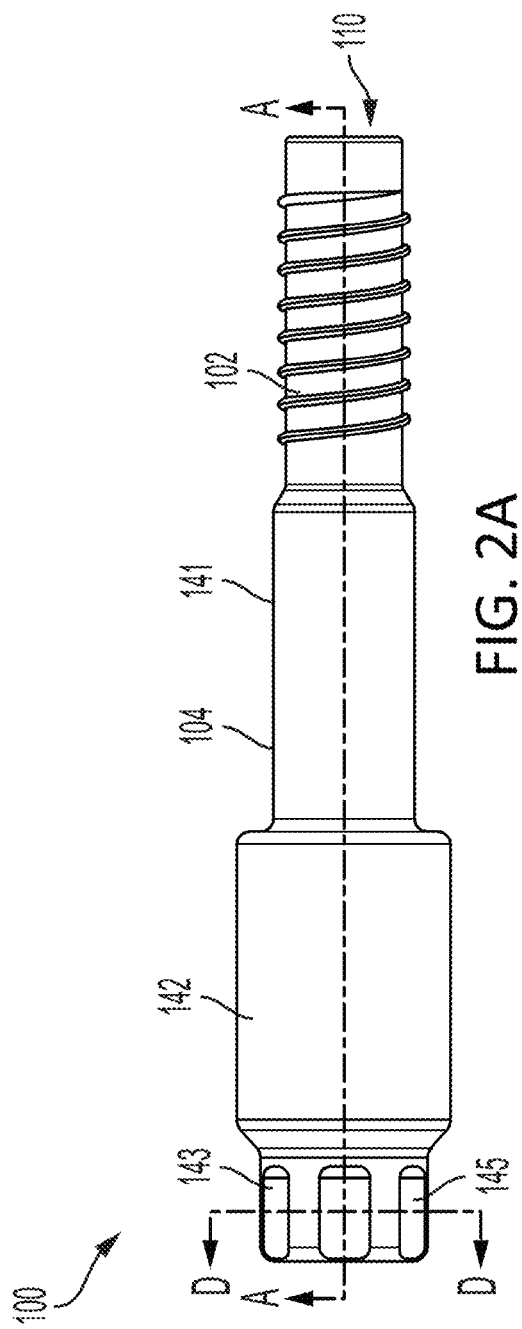
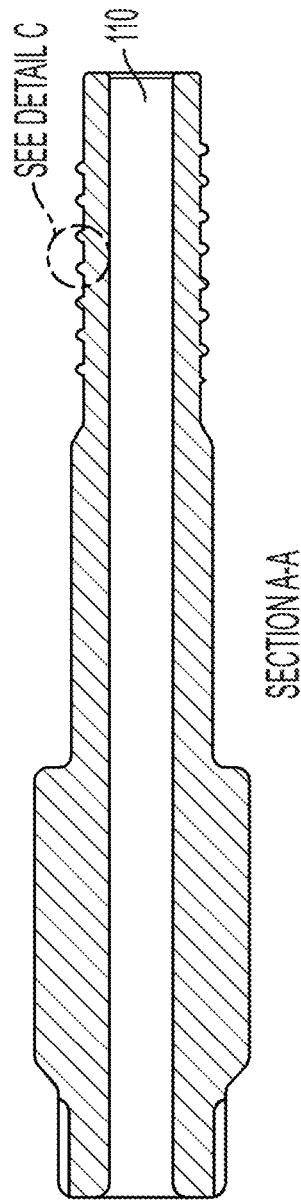
FIG. 2A
FIG. 2B
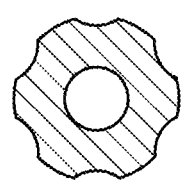
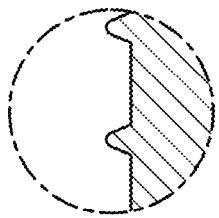

CRANIAL ACCESS DEVICE

FIELD OF THE DISCLOSURE

The present disclosure generally relates devices and methods for gaining access to the interior of human and animal brains. Specifically, the disclosure relates to cranial bolts or screws for securing medical devices to the skull and for providing access to an interior of the skull, and methods of operation thereof.

BACKGROUND OF THE DISCLOSURE

Cranial access devices such as cranial bolts are used to secure medical devices to the head and control the depth and/or trajectory of such medical devices inserted into the brain within the skull. The medical devices can include, for example, catheters, neurosurgical tools, probe drivers, or probes. The medical device is introduced into a lumen or hole of the access device and into a corresponding hole in the skull.

The medical device is secured to the skull by threading the cranial access device into the cranium and then attaching or coupling the medical device to the cranial access device. For example, an interventional procedure on the subject's brain may involve drilling a burr hole into a subject's skull, mounting a cranial access device on the subject's skull, and guiding an instrument (e.g., a catheter, a needle, a cannula, an electrode, or other device) to the desired target within the subject via the cranial access device, such as by using pre-operative or live images from an imaging modality (e.g., MR, CT, PET, ultrasound, etc.) in an image-guided procedure. Accurate guidance is desirable, particularly for an interventional procedure on the brain, where millimeter or sub-millimeter accuracy of the instrument location may be desirable. However, current access devices are made from conductive materials including metals (e.g., titanium) that can induce artifacts during imaging (e.g., magnetic resonance imaging (MRI), thermography, etc.), particularly when used during treatment of shallow targets such as <20 mm from the skull surface. This impacts an operator's ability to visualize the medical device and/or the image guided therapy during treatment.

The current disclosure describes devices and methods directed towards solving some of the issues discussed above.

SUMMARY OF THE DISCLOSURE

Disclosed scenarios provide a cranial access device that reduces or eliminates artifacts during imaging. The cranial access device includes a cranial bolt and a drive adapter. The cranial bolt may include a distal threaded portion, a proximal drive portion comprising a plurality of protrusions that form an external drive geometry, and a central passageway configured for receiving a neurosurgical tool. The drive adapter may include a distal end configured to receive and interface with the external drive geometry of the proximal drive portion, and a proximal end configured to receive a driver tool. In some scenarios, a kit for use during neurosurgery is disclosed that includes the cranial access device and a driver tool, where the driver tool is inserted into the cranial access device to provide a continuous lumen for insertion into a stereotactic device during a surgical procedure Optionally, the cranial bolt is manufactured using a non-conductive, rigid material that substantially reduces formation of artifacts during magnetic resonance imaging such as, without limitation ceramic.

In one or more embodiments, the drive adapter can be manufactured using a semi-rigid material such as without limitation plastic.

In various scenarios, the distal threaded portion may be configured for self-tapping of the cranial bolt into a skull hole. In such scenarios, the distal threaded portion can include a distal end that does not include threads.

In various embodiments, the cranial access device may also include at least one reducing tube for modifying a diameter of the central passageway.

Optionally, the central passageway may be further configured to receive at least a portion of a drive pin of the drive tool.

Additionally and/or alternatively, a first outer diameter of a section of the cranial bolt between the proximal drive portion and the distal threaded portion may be substantially equal to an outer diameter of the drive adapter. In such embodiments, a second outer diameter of a second section of the cranial bolt between the proximal drive portion and the distal threaded portion may be less than the first outer diameter.

Optionally, a torque tolerance of the drive adapter may be less than a torque tolerance of the cranial bolt.

BRIEF DESCRIPTION OF THE DRAWINGS

FIG. 2A illustrates an example cranial bolt of the cranial access device of FIG. 1.

FIG. 2B is a cross-sectional view of the cranial bolt of FIG. 2A.

BRIEF DESCRIPTION OF DISCLOSED EMBODIMENTS

Figure 1:
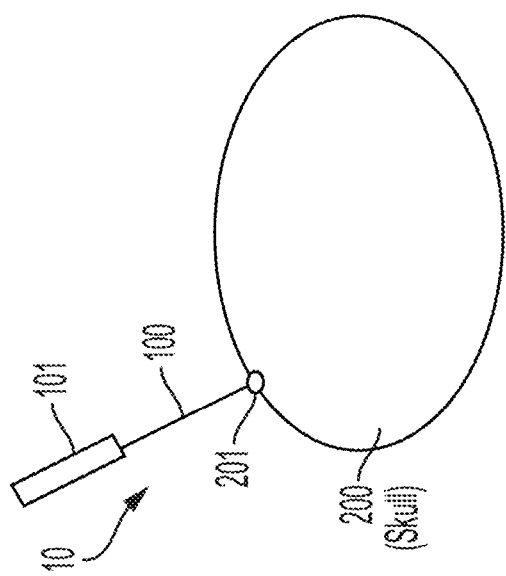
FIG. 1 is an elevation view of the cranial access device of the present invention installed in a patient's skull.

The devices and methods of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, proximal, distal, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". It should be noted that the terms "proximal" and "distal" as used herein, are intended to refer to a direction toward (proximal) and away from (distal) a surgeon or other user of the device.

While the examples provided in this disclosure generally relate to bolts or screws for cranial access, disclosed systems and methods of this disclosure may be used for any other bone through which it is desirable to pass a catheter or other similar device, such as, but not limited to, the spinal vertebrae, hip, or the like. For example, disclosed embodiments may be used for access to the vertebral body of the spinal vertebra without deviating from the principles disclosed herein.

Cranial bolts are commonly utilized in holes (e.g., burr holes, twist holes, etc.) in the skull of a patient for subsequent medical device placements (e.g., catheter, electrodes, neurosurgical tools, probe drivers, probes, etc.). The cranial bolt of the current disclosure provides for artifact free and/or substantially artifact free visualization of medical device(s), medical device trajectory (e.g., using a fiducial marker without penetrating the tissue), image guided therapy in proximity of the medical device, and/or the tissue in proximity of the medical device during neurosurgical procedures as well as other imaging procedures. Embodiments may be used with dedicated medical devices or systems that are designed anew, or with preexisting systems. For example, embodiments may be used with medical devices or systems like the ones shown in U.S. Pat. Nos. 9,510,909 and 10,327,830, the disclosures of which are incorporated herein by reference in entirety.

The devices and methods disclosed herein aim to improve upon at least one of the aforementioned problems. However, it shall be understood that the disclosure herein is not limited to merely solving these specific problems. Additionally, while the devices and techniques disclosed herein are described with respect to a human body or patient, it is understood that the devices and techniques may in suitable circumstances be applied to a non-human patient (i.e., in veterinary medicine).

In various implementations, the current disclosure describes a cranial access device including a cranial bolt and drive adapter assembly. The cranial bolt is manufactured using a non-conductive (e.g., non-electrically conductive) material that does not introduce (and/or introduces minimal) artifacts during imaging such as, without limitation, ceramic, fiberglass, plastic, glass filled polymers, or the like. Furthermore, the material may be chosen such that it is harder than bone and allows for self-tapping of the cranial bolt. The cranial bolt is configured to be inserted into a hole formed in a subject's skull, and for allowing a medical device to access the cranial cavity, via the cranial bolt.

Typically, the hole is drilled into a patient's skull using a twist drill and a threaded portion of the cranial bolt is screwed directly into the hole. Other prior art bolts may require the additional step of tapping or threading the hole to provide threads in the skull so the prior art bolt can engage the skull. The current cranial bolt, however, is self-tapping, so it does not require the additional step of tapping the hole. Ceramic cranial bolts may exhibit increased risk of fracture when driven by a tool (e.g., an insertion driver) during insertion into the skull hole due to the low compliance between the two materials that increases point-load stress concentrations. The drive adapter of the current disclosure provides an interface between a driving tool and the cranial bolt during insertion of the cranial bolt in the skull hole by engaging a proximal end of the cranial bolt, and is configured to improve fracture resistance of the cranial bolt by, for example, distributing the load between the drive adapter and the cranial interface. Optionally, the drive adapter may also be configured to act as a torque limiter such that the drive adapter fails (e.g., fractures) before the torque tolerance of the cranial bolt is achieved during insertion.

A medical device may be guided through a contiguous lumen (having a uniform diameter, a stepped diameter, etc.) of the cranial bolt and the drive adapter for accessing the cranium of the subject. For example, a proximal end of the bolt is sized to accept an instrument for neurological intervention that can access the target tissue through the distal end of the bolt (with or without the drive adapter attached thereto). Optionally, the proximal end of the bolt is dimensioned in a manner such that multiple bolts can be placed in close proximity of one another. The distal end of the bolt is designed in a manner such that an internal opening (i.e., an internal diameter) at the distal end of the bolt is configured to receive various instruments. Additionally, the outside diameter of the distal end of the bolt may be configured to prevent injuries to the skull, and minimize the diameter of the drilled hole in the skull of the subject.

Referring now to the drawings, and in particular to FIGS. 1-6, an example cranial access device 10 is shown and described. The cranial access device 10 can be used to facilitate a medical device to access the cranial cavity of a subject. Specifically, the cranial access device 10 is a rigid skull fixation device that is designed to provide a stable platform for inserting, attaching, or otherwise coupling medical devices or instruments within a subject. Referring to FIG. 1, a cranial access device 10 including a cranial bolt 100 and a drive adapter 101 is illustrated secured to a skull 200 of a patient, according to the present disclosure.

As shown in FIG. 2A, a cranial bolt 100 includes a distal threaded portion 102 and a proximal non-threaded portion 104. A central passageway 110 extends through the length of the cranial bolt 100 (i.e., between the distal end and the opposing proximal end) and is illustrated having a circular cross section, but can be any geometric shape, e.g. triangle, square, hexagon, and pentagon (not illustrated). Further, as shown in FIG. 2B, the central passageway 110 has a uniform diameter or width throughout its length. While not shown in FIG. 2B, the diameter of the central passageway may be stepped and/or may uniformly increase from the distal end to the proximal end. While the cranial bolt is illustrated as a one-piece construction, it may, optionally, include 2 or more pieces coupled together.

Figure 3:
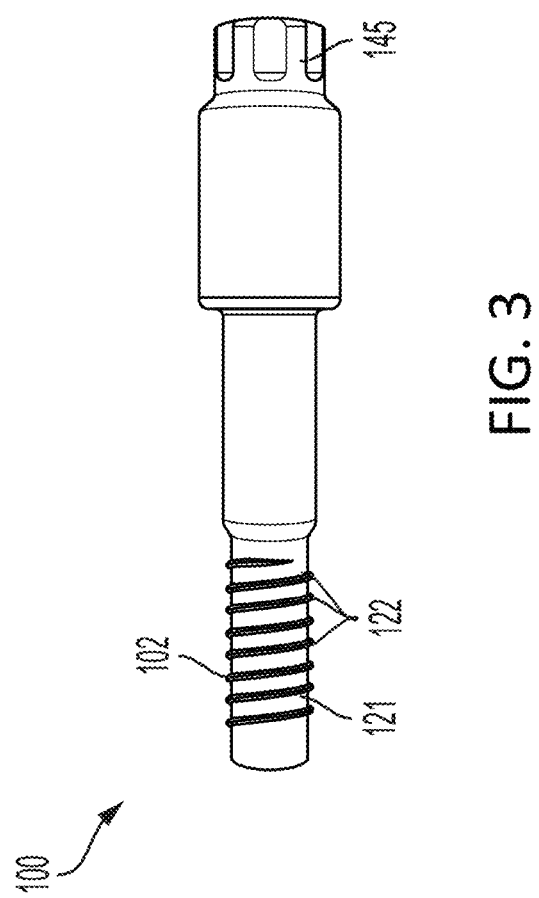
FIG. 3 is an enlarged view of a threaded portion of the cranial bolt of FIG. 2A.

Referring now to FIG. 3, threaded portion 102 has an outer surface 121 with a plurality of threads 122 for engaging a hole 201 formed in skull 200 to fixedly engage threaded portion 102 to skull 200 (by self-tapping). Typically, a hole is drilled into a patient's skull using a twist drill.

In one optional embodiment, hole 201 is tapped, or threaded to provide threads for threaded section 102 to engage the skull. In various other embodiments, threaded portion 102 and threads 122 are self-tapping and do not require the additional step of tapping hole 201. For example, the self-tapping threaded portion 102 includes tapered threads configured to start threading and then pulling the bolt into the hole 201. Optionally, self-tapping ability may be created by cutting a gap in the continuity of the thread, generating a flute and cutting edge. Self-tapping threaded portion 102 reduces the number of steps required and decreases the amount of time required for a given procedure.

Optionally, the distal tip of the threaded portion 102 may be tapered or blunted to a diameter less than that of the major thread diameter of the threads 122 to aid in engagement of the initial thread with the skull and maintain a desired trajectory alignment. This may be particularly useful for holes that are angled away from a perpendicular axis of the skull.

Additionally and/or alternatively, the distal end of the threaded portion 102 may not include any threads to provide the ability of inserting the bolt into the skull of the subject in a seamless manner (e.g., when the wall thickness of the threaded section is too thin to use a fully threaded distal end). For instance, a distal end of the threaded portion 102 (e.g., about 1 mm to about 5 mm, about 2 mm to about 4 mm, about 1 mm, about 2, mm, about 3 mm, about 4 mm, about 5 mm, etc. in length from the distal tip) may be unthreaded. The diameter of this unthreaded portion may approximately be equal to the minor diameter of the threads 122. This allows the bolt to enter the drill hole slightly before the threads start to engage. Constraining the tip portion of the bolt within the hole keeps the bolt aligned and improves the ability of the first thread to 'catch.' This helps maintain the desired trajectory and generally improves the ability to thread the bolt into the hole. Furthermore, when a trajectory of inserting the bolt into the skull of the subject is inclined to skull surface, the bolt must be inserted into an angled hole, wherein the threads must "catch" (i.e. engage) to the skull surface, thereby provisioning the bolt to be threaded into the skull in a seamless manner. The unthreaded portion distal tip provisions for such an insertion of the bolt tip into the hole, thereby guiding the bolt before the threaded portion engages with the skull surface.

The bolt 100 is manufactured using a material that is harder than bone, is not electrically conductive, and/or does not introduce (or substantially reduces) artifacts during imaging (e.g., being non-ferrous, having low electrical conductivity) such as, without limitation, ceramic, fiberglass, plastic, glass filled polymers, or the like. Example ceramic compositions can include, without limitation, Zirconia (e.g., yttria partially stabilized zirconia, hipped yttria partially stabilized zirconia, etc.), zirconia-toughened alumina, alumina (e.g., AD-96%, ADO-96%, etc.), porcelain, steatite, cordierite, or the like.

Figure 4B:
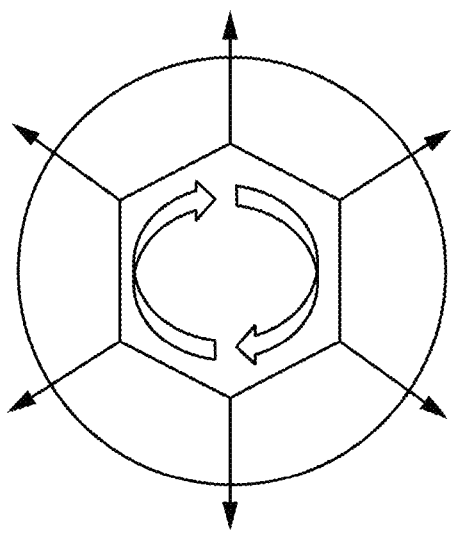
FIG. 4B illustrates tensile forces on an internal drive geometry.
Figure 4A:
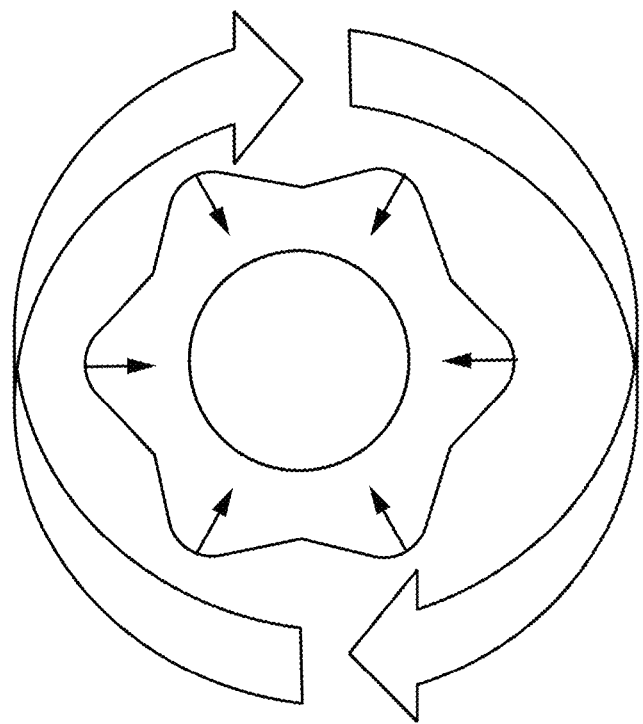
FIG. 4A illustrates compressive forces on an external drive geometry.
Figure 4C:
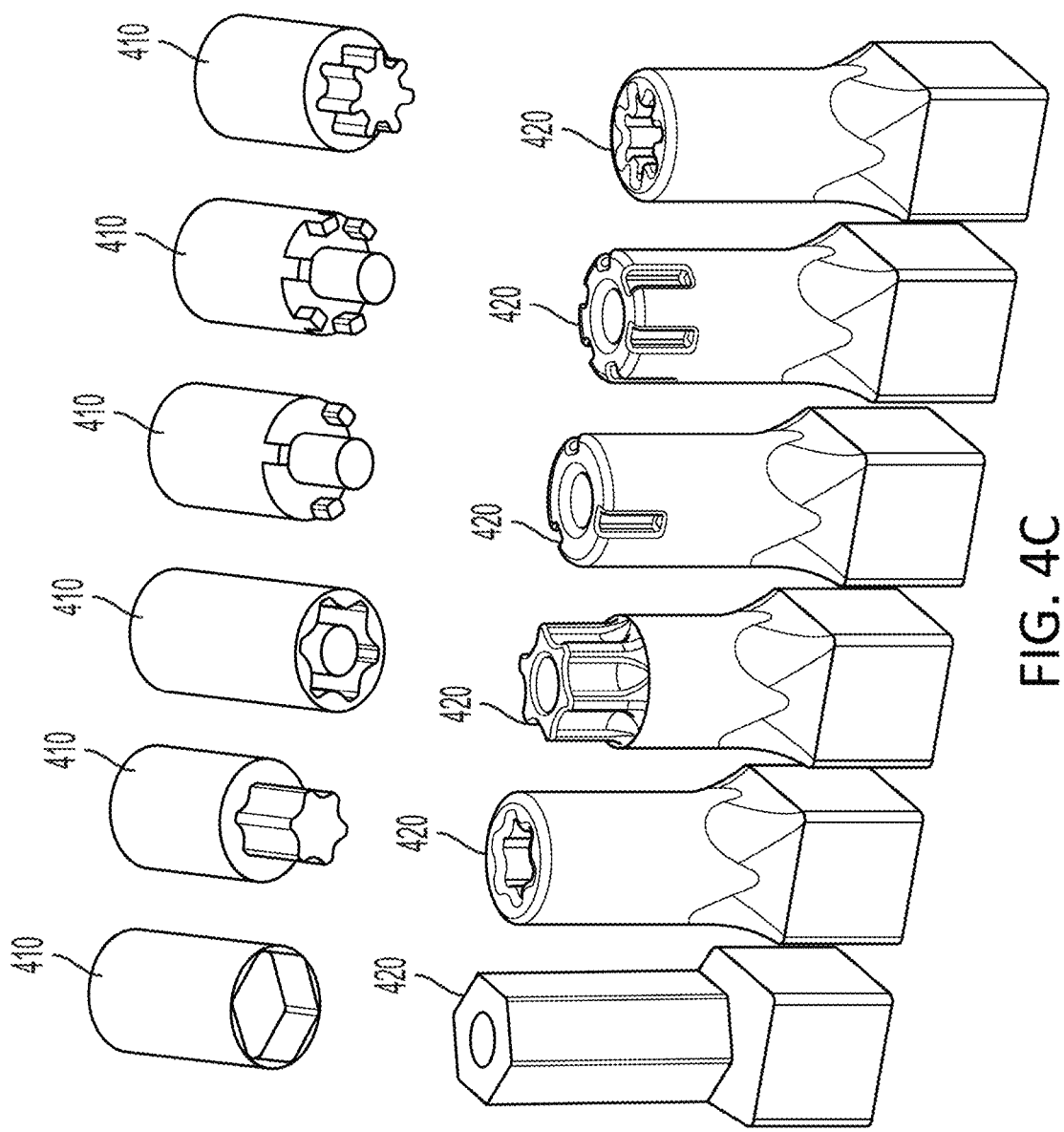
FIG. 4C illustrates example external drive geometries.

As shown in FIG. 2A, the non-threaded portion 104 may include a first cylindrical section 141, a second cylindrical section 142, and a driver section 143. The first and second cylindrical sections 141 and 142 have relatively smooth outer surfaces, where a diameter of the outer surface of the second cylindrical section 142 is greater than that of the first cylindrical section 141. The change in diameter allows for formation of a "shoulder" between the first cylindrical section 141 and the second cylindrical section 142 that facilitates an edge for affixing a medical device (e.g., probe or probe driver) securely to the bolt. The drive section 143 includes protrusions 145 that form an external drive geometry in the form of, for example, a sinusoidal pattern as shown in FIG. 4A. Ceramics and other similar materials tend to be weaker under tension forces than they are under compressive forces. An external drive geometry allows the proximal end of the bolt 100 to be under compressive forces as shown in FIG. 4A (instead of the tensile forces shown in FIG. 4B) during installation and/or removal of the bolt 100 from the skull hole, thereby reducing the risk of fracture or breakdown of the bolt 100. Additionally, the sinusoidal pattern may be selected to minimize sharp edges which can cause stress concentrations leading to fracture or breakdown of the bolt 100. However, other patterns of protrusions 145 such as wave patterns with rounded lobes or protrusions around the rim of the central passageway where the number of lobes can be 3, 4, 5, or the like, are within the scope of this disclosure. Examples of such patterns are shown as 420 in FIG. 4C.

According to an embodiment, a total length of the cranial bolt 100 between the proximal end and the distal end is about 35 mm to about 45 mm, about 37 mm to about 43 mm, about 38 mm to about 42 mm, about 40 mm, about 41 mm, about 42, or the like. The length of the threaded portion 102 is about ¼ to about ½ of the length of the cranial bolt, about ¼ of the length of the cranial bolt, about ⅓ of the length of the cranial bolt, about ½ of the length of the cranial bolt, or the like. The diameter of the central passageway is about 1.5-4.5 mm, about 2-4 mm, about 3 mm, about 1.5 mm, about, 2 mm, about 2.2 mm, about 2.5 mm, about 3 mm, about 3.3 mm, about 3.5 mm, about 4 mm, about 4.5 mm, or the like. The outside diameter of the threaded portion 102 is about 5.5 mm to about 7 mm, about 5.7 mm to about 6.7 mm, about 6 mm to about 6.5 mm, about 5.5 mm, about 6 mm, about 6.3 mm, about 6.5 mm, about 6.8 mm, about 7 mm, or the like; inside diameter of the threaded portion 102 is about 3.5 mm to about 5.5 mm, about 4 mm to about 5 mm, about 4.2 mm to about 4.8 mm, about 3.5 mm, about 4 mm, about 4.2 mm, about 4.5 mm, about 4.8 mm, about 5 mm, about 5.5 mm, or the like; while the pitch of the threaded portion 102 is about 0.75 mm to about 1.5 mm, about 1 mm to about 1.25 mm, about 0.75 mm, about 1 mm, about 1.25 mm, about 1.5 mm, or the like. The outer surface diameter of the (i) first cylindrical portion 141 is about 5 mm to about 6.5 mm, about 5.2 mm to about 6.3 mm, about 5.4 mm to about 6.1 mm, about 5.6 mm to about 5.9 mm, about 5 mm, about 6.5 mm, about 5.2 mm, about 6.3 mm, about 5.4 mm, about 6.1 mm, about 5.6 mm, about 5.7 mm, about 5.8 mm, about 5.9 mm, or the like; (ii) the second cylindrical portion 142 is about 7 mm to about 9.5 mm, about 7.5 mm to about 9 mm, about 8 mm to about 8.5 mm, about 7 mm, about 7.5 mm, about 8 mm, about 8.5 mm, about 9 mm, or the like; and (iii) the drive portion 143 is about 5 mm to about 6.5 mm, about 5.2 mm to about 6.3 mm, about 5.4 mm to about 6.1 mm, about 5 mm, about 6.5 mm, about 5.2 mm, about 6.3 mm, about 5.4 mm, about 6.1 mm, about 5.8 mm, about 5.9 mm, about 6 mm, or the like, respectively. It must be appreciated that each of the above described exemplary dimensions can be varied as long as the resultant bolt is not inconsistent with the description herein.

While not shown here, the first cylindrical portion 141 and/or the second cylindrical portion 142 may include marked gradations. For example, the markings can indicate a scale in millimeters such that a marking is provided every millimeter. However, markings for other units of measurement, such as centimeters, inches, and the like are within the scope of this disclosure.

A medical device (e.g., a neurosurgical device such as a probe) can be inserted into central passageway 110 for access to target tissue and be held in place by friction, compression fitting, or the like. For example, the central passageway 110 of the bolt 100 is sized to accept an instrument or a medical device for neurological intervention at the proximal end and that can access the target tissue through the distal end of the bolt 100. Optionally, for medical devices that have a diameter that is less than that of the central passageway 110 such that they cannot be held in place by friction or compression fitting (e.g., biopsy needles, SEEG electrodes, catheters, etc.), the cranial access device 10 may include a reducing tube that is configured for insertion into the central passageway 110 so as to reduce the diameter of the central passageway for receiving the medical device. The internal diameter of the reducing tube may be configured for receiving a medical device. Optionally, a sealing gasket maybe associated with the outside of the reducing tube (e.g., at the proximal end) in order to minimize fluid (e.g., cerebrospinal fluid) leakage and/or to retain the desired position of the inserted medical device. The reducing tube may also be made from a non-conductive material that presents minimal artifacts during imaging such as, without limitation, ceramic, fiberglass, plastic, etc.

The proximal end of the bolt is dimensioned in a manner such that multiple bolts can be placed in close proximity of one another. The distal end of the bolt is designed with an internal opening (i.e., diameter of the central passageway at the distal end) such that the distal end can receive instruments having dimensions of about 4-5 mm or less in diameter. However, the disclosure is not so limiting, and larger diameters of the central passageway are within the scope of this disclosure (e.g., up to about 14 mm). According to an embodiment, the threaded portion 102 of the bolt 100 can be sized to self-tap into holes having a diameter of about 3 mm to about 8 mm, about 4 mm to about 7 mm, about 5 mm to about 6 mm, about 3 mm, about 3.5 mm, about 4.5 mm, about 5.5 mm, about 6 mm, about 6.5 mm, about 7 mm, about 8 mm, or the like.

Figure 5C:
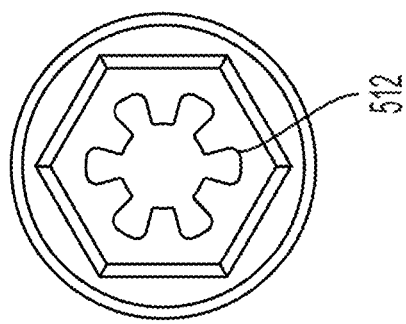
FIG. 5C illustrates a cross-sectional view of the drive adapter of FIG. 5A at a proximal end.
Figure 5A:
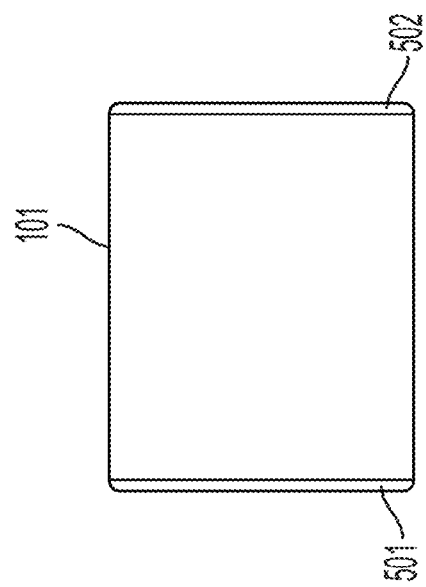
FIG. 5A illustrates an example drive adapter of the cranial access device of FIG. 1.

Referring now to FIG. 5A, the drive adapter 101 engages the drive section 143 at the proximal end of the cranial bolt 100, and provides an interface between a driving tool 600 and the cranial bolt 100 during insertion of the cranial bolt 100 in the skull hole. As discussed above, cranial bolts made from ceramic or other such rigid materials may exhibit increased risk of fracture when driven by a driver tool during insertion into and/or removal from the skull hole because the two rigid materials of the cranial bolt and the driver tool tend to concentrate loads on single points leading to premature damage because of stress concentrations. An intermediary drive adapter 101 between the cranial bolt and the driver tool that is manufactured using less rigid materials such as plastic, fiberglass, or the like can help absorb some of the stress concentrations (e.g., by frictional interference) to improve fracture resistance of the cranial device. Additionally and/or alternatively, the drive adapter may be configured to act as a torque limiter by "stripping out" at a lower torque limit compared to the ultimate failure torque of the cranial bolt.

Figure 5B:
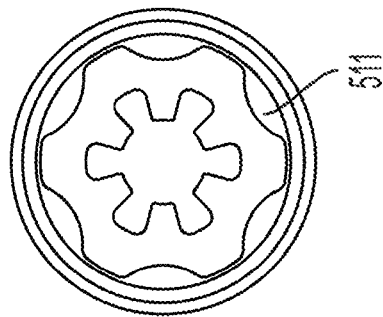
FIG. 5B illustrates a cross-sectional view of the drive adapter of FIG. 5A at a distal end.

As shown in FIGS. 5A, 5B, and 5C, the distal end 501 of the drive adapter 101 includes an inner surface profile 511 that is complementary in shape to the outer drive geometry (e.g., complementary to the sinusoidal pattern discussed above and/or to the patterns 420 shown in FIG. 4C illustrated as 410) of the drive portion 143 of the cranial bolt 100. Moreover the diameter of the inner surface profile 511 is configured such that the drive portion 143 can be inserted into the distal end 501 of the drive adapter 101 and retained therein by compression fitting or friction. The proximal end 502 of the drive adapter 101 includes an inner surface profile 512 that is complementary in shape to the driver tool. Moreover the diameter of the inner surface profile 512 is configured such that the driver tool can be inserted into the proximal end 502 of the drive adapter 101 and retained therein by compression fitting or friction. In various embodiments, a length of the drive adapter may be about 8 mm to about 12 mm, about 9 mm to about 11 mm, about 8 mm, about 9 mm, about 10 mm, about 11 mm, about 12 mm, or the like. An outer diameter of the drive adapter may be about 6 mm to about 10 mm, about 7 mm to about 9 mm, about 8 mm, about 6 mm, about 7 mm, about 9 mm, about 10 mm, or the like.

Figure 6:
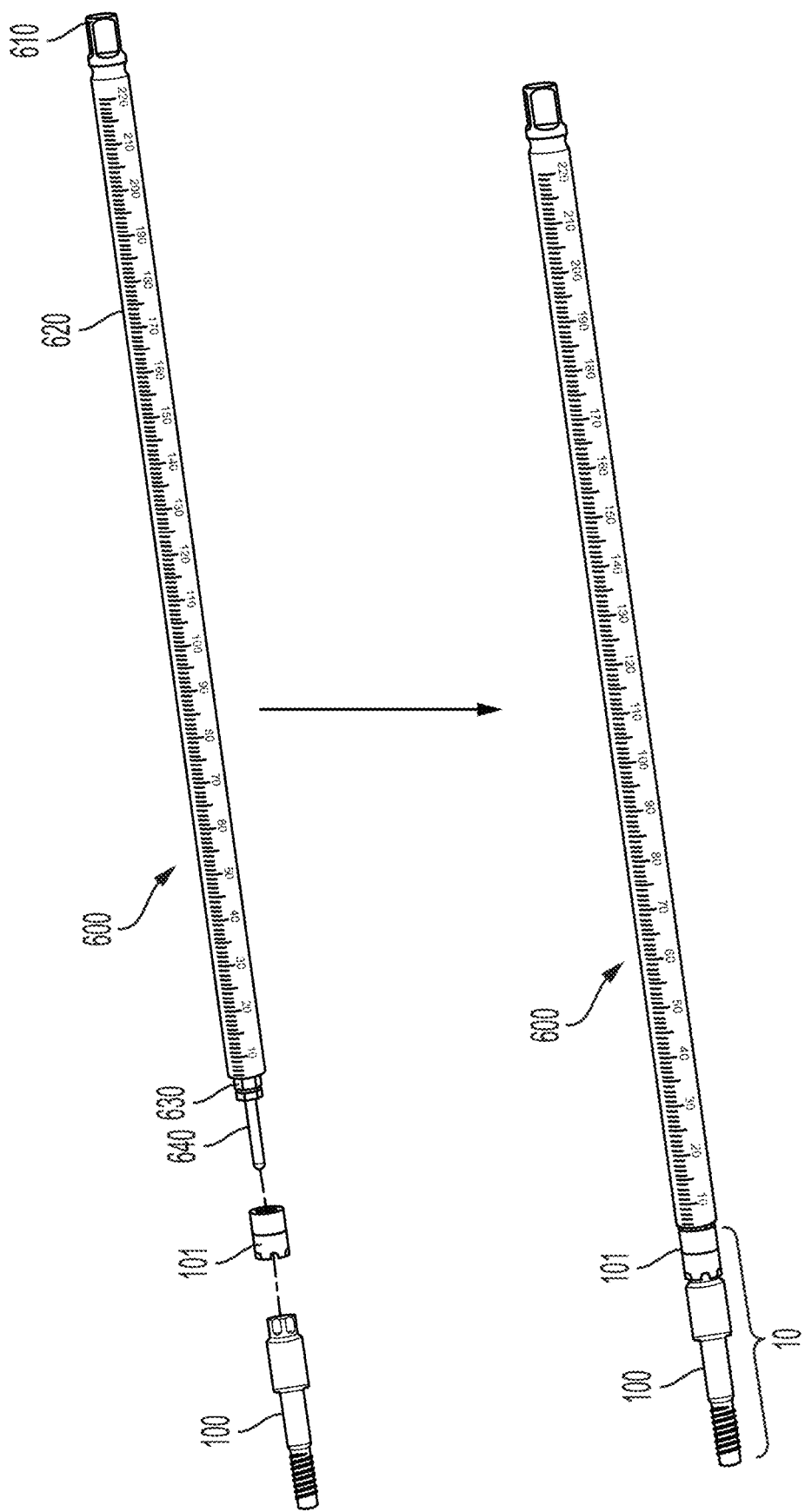
FIG. 6 illustrates an example driver tool before and after being coupled to a cranial access device including a ceramic bolt and a drive adapter.

For example, FIG. 6 illustrates an example driver tool 600 that can be used to attach the above described cranial access device 10 to the skull of a subject. Referring to FIG. 6, the driver tool 600 includes a driver head 610 (e.g., ridged) and a shaft 620. The driver head 610 affixes into a driver handle (not shown here) that enables rotating the driver in order to affix the bolt to the skull. Optionally, the shaft may include markings or gradations. As shown, the driver tool 600 includes a ridged portion 630 that is disposed at a distal end of the shaft 620. The distal end of the shaft is the end that is away from the head 610. The ridged portion 630 is configured to be inserted into the proximal end 502 of the drive adapter 101. The distal end of the driver tool also includes drive pin 640 affixed to the ridged portion 630. In various embodiments, the drive pin 640 is configured to have a length longer than a length of the drive adapter 101 such that the drive pin 640 is at least partially received within the central passageway 110 of the bolt 100. The drive pin 640 may engage with the central passageway 110 of the bolt 100 to aid in alignment with the desired trajectory.

The ridged portion 630 of the shaft enables the affixing/removing of the bolt 100 from the skull of the subject, via the drive adapter 101. Specifically, the driver 600 can be inserted into the drive adapter 101 having an opening that is of a similar shape as that of the ridged portion 630 of the driver. In doing so, the driver 600 can engage with the bolt 100 via the drive adapter 101 and impart a torque to drive the bolt into the skull of the subject.

An exemplary process of using the cranial access device 10 in a surgical procedure includes inserting ridged portion 630 of the shaft of the driver tool 600 into the proximal end 502 of the drive adapter 101, while the distal end 501 of the drive adapter 101 interfaces with the drive portion 143 in the top of the bolt 100. The threaded portion 102 of the bolt 100 is aligned with a pre-drilled hole in the skull. As the threaded portion 102 is self-tapping, the handle of the driver 600 can be used to turn the bolt 100, via the intermediate drive adapter 101 in a first direction (for example, clockwise) to thread the bolt 100 into the pre-drilled hole. Upon the bolt 100 being threaded into the skull by a sufficient distance, the driver tool 600 may be removed.

A medical device (e.g., a probe) may be attached to the bolt directly and/or via the driver by, for example, insertion into the central passageway of the bolt (and, optionally, the shaft of the driver), and further feeding the medical device through the bolt into the skull. Additionally, after the surgical process is complete, the bolt may be removed from the skull by reinserting the driver tool and turning the handle of the driver tool to thereby turn the bolt in a second direction (counter clockwise, for example) opposite to the first direction.

In various embodiments, the outer diameter of the second cylindrical section 142 of the cranial bolt 100, the outer diameter of the drive adapter 101, and the outer diameter of the shaft 620 of the driver tool 600 are approximately the same such that the cranial access device 10 with the driver tool 600 form an assembly that has a continuous diameter, thereby allowing the assembly to pass through a stereotactic instrument that is used to align the trajectory of the bolt. It must be appreciated that the above described cranial access device (with or without the driver tool) have a configuration that provision for seamless integration of surgical instruments, which can be used for general surgical purposes or for a specific purpose, and optionally be prepackaged or assembled together for insertion into a stereotactic device (e.g., via back loading). Such a configuration allows for ease of useability by reducing the number of steps an operator has to perform for assembling the medical access device and the driver tool before insertion into a stereotactic instrument for use in a seamless manner in a surgical procedure. The continuous diameter of the bolt and drive adapter also allows the bolt to be inserted through a stereotactic instrument aligned on a trajectory to the target and thus allows the stereotactic instrument to be placed at any reasonable distance from the skull. If, for example, the bolt was of a larger diameter than the drive adapter, it would need to be held between the skull and stereotactic instrument to allow drive adapter to first pass through stereotactic instrument and then engage bolt. This would, in turn, require a user to ensure that the distal portion of stereotactic instrument is located sufficiently far away from skull to fit the length of the bolt thereby complicating the setup. Therefore, the present disclosure provides for an apparatus and corresponding methods that provide a stable platform for the introduction of surgical, therapeutic or diagnostic intervention into the central nervous system (CNS), and in particular into the brain of a mammalian subject. The apparatus provides stereotactic guidance for the placement and fixation of instruments for use in neurological procedures, and in particular for neurological procedures that are performed in conjunction with preoperative or perioperative monitoring such as magnetic resonance imaging (MRI) or computed tomography (CT) imaging. Moreover, the apparatus of the present disclosure is made from a material that is compatible with MRI or CT imaging systems.

Figure 7A:
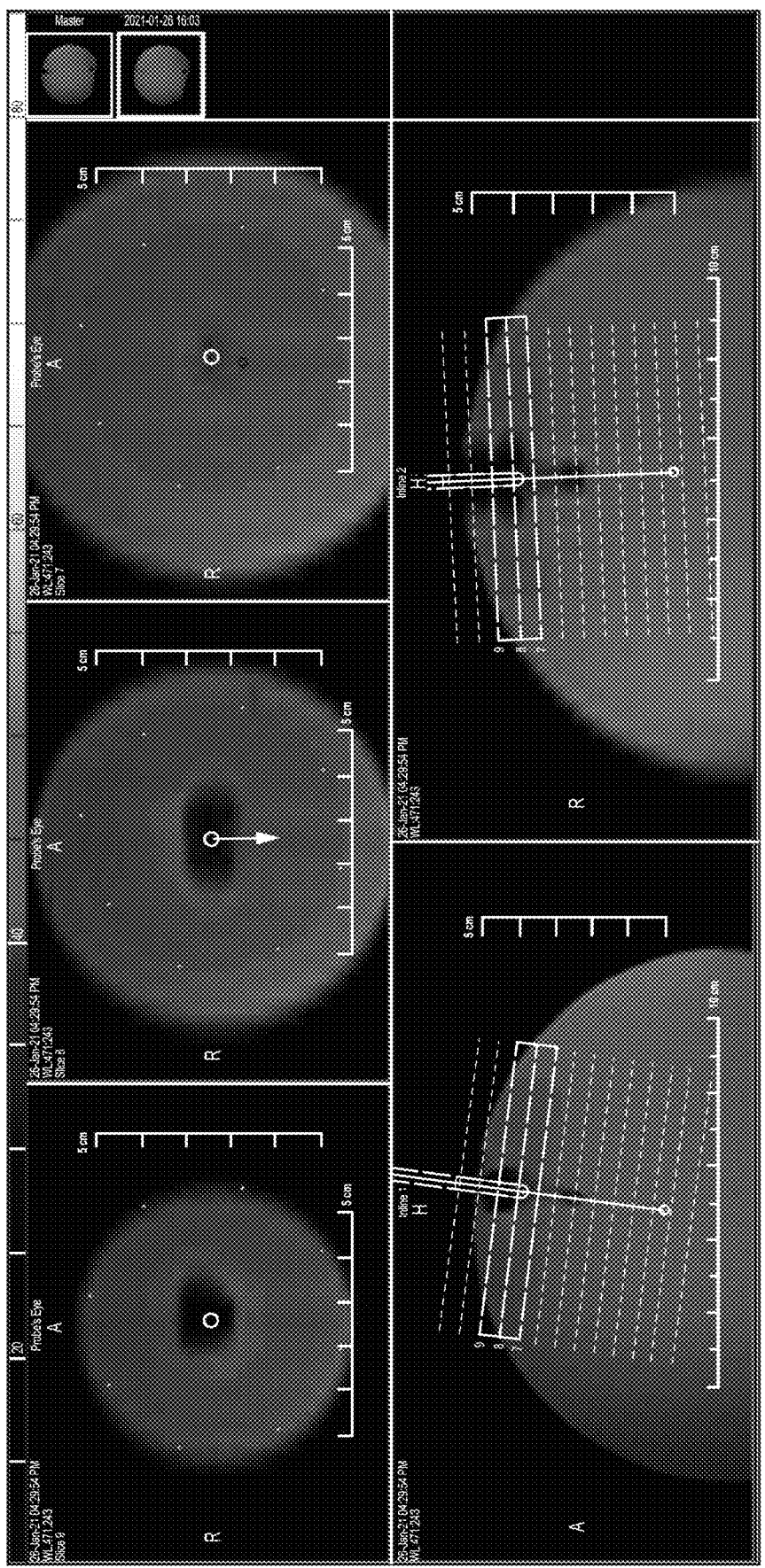
FIG. 7A illustrates artifacts introduced in images with metallic cranial bolts.
Figure 7B:
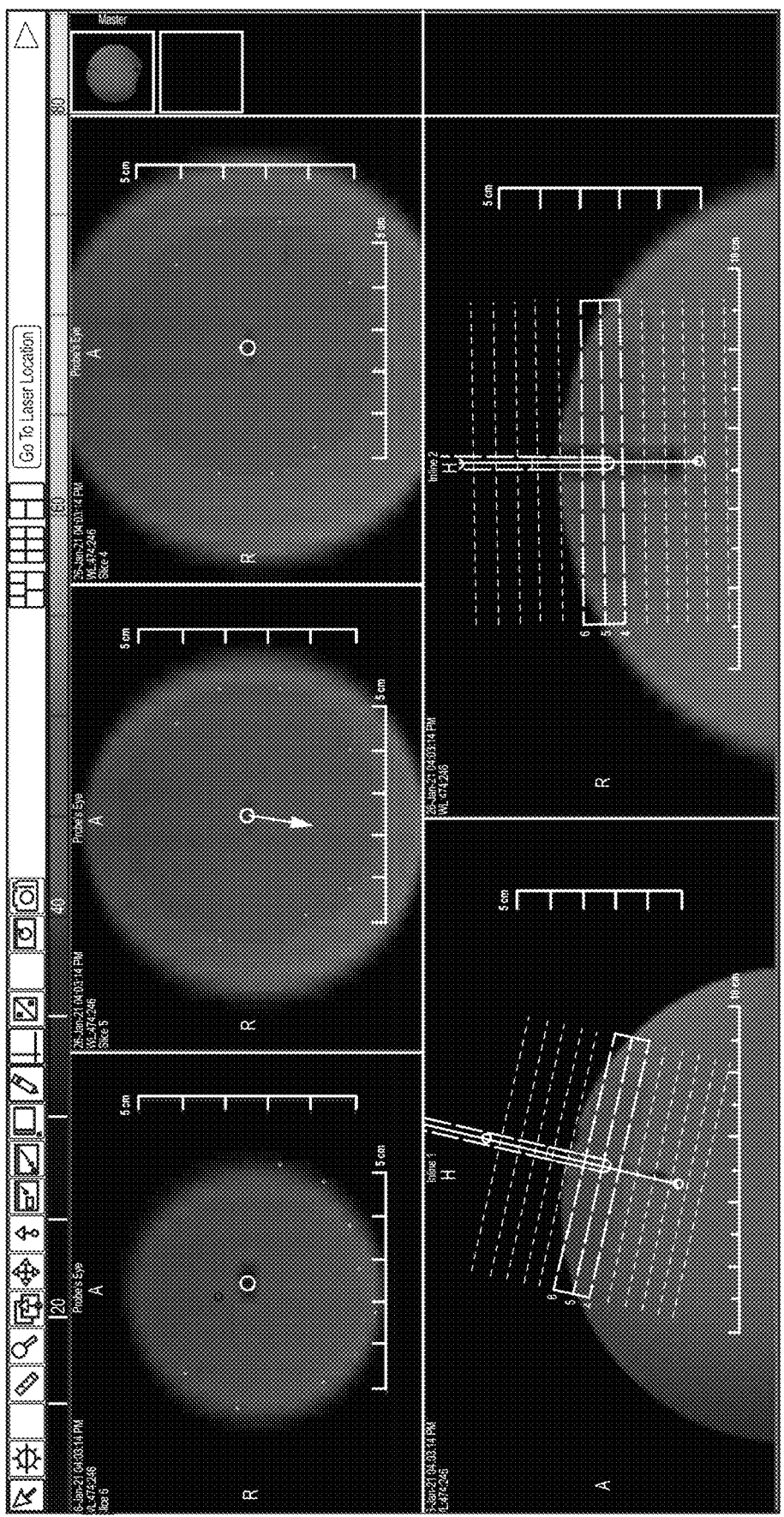
FIG. 7B illustrates images with the cranial bolt of the current disclosure that include substantially reduced or no artifacts.

In addition to being compatible with the various imaging systems, the material of the cranial bolt is selected to reduce or eliminate artifacts during imaging. For example, FIG. 7A illustrates artifacts in the images when a metallic cranial bolt is used compared to the images with the cranial access device of the current disclosure that do not include and/or substantially reduce or eliminate such artifacts (FIG. 7B).

According to an embodiment, the cranial access device 10 (including the bolt 100 and the drive adapter 101) has a slim profile, thereby allowing multiple bolts to be inserted into the skull at multiple trajectories that are within close proximity of one another. The skull mounted bolt is robust, accurate, and provides a seamless way to provide stereotactic guidance, placement and fixation for the operation of instruments or devices. Additionally, the bolt is MRI compatible, does not create substantial artifacts during imaging, and has a slim fit to allow multiple trajectories.

According to one embodiment, the dimensions of the cranial access device 10 allow the device to be placed in close proximity to one or more other similar devices. This feature provides the advantageous ability of using multiple apparatus in contiguous/non-contiguous regions in a single treatment session. Accordingly, the ability of the medical provider to apply therapeutic intervention to a larger area of the CNS (e.g., the brain) in a single session is maximized. For instance, a single therapeutic session may include 2-10 skull mounted bolts (preferably 2-5 bolts) that are disposed within close proximity of one another. While employing multiple bolts, the inter-bolt separation is required in order to accommodate, for instance, a probe driver or a probe adapter that may be positioned over the connector portion of the bolt. Furthermore, by providing a sufficient spacing between the bolts, also provisions the surgeon with easy access to the individual bolts, as well as regions of the skull around the bolt.

According to an embodiment, the above discussed skull mounted bolts (and cranial access devices) are MRI compatible. Two or more bolts can be used in a single therapeutic session that takes place within an imaging apparatus. Accordingly, a further aspect of the present disclosure provides for methods of treating living subjects, such as human or other mammalian subjects, using a magnetic field in a magnetic resonance volume.

By one embodiment, the magnet can be positioned relative to the subject so that the magnetic resonance volume, at least partially encompasses a region of the subject to be treated. A movable applicator adapted to apply energy within an energy application zone is positioned relative to the subject so that the energy application zone intersects the magnetic resonance volume within the region of the subject requiring treatment. While the static field magnet is applying the static magnetic field in the magnetic resonance volume, radio frequency signals are applied so as to elicit magnetic resonance signals from tissues of the subject in the magnetic resonance volume. The method also includes receiving these magnetic resonance signals and deriving magnetic resonance information relative to the subject's tissues in the magnetic resonance volume from the magnetic resonance signals.

According to one embodiment, the skull mounted bolts or cranial access devices described above can be used in conjunction with a robotic probe driver. The robotic probe driver can align and position a tip of the probe at a certain distance from a target area (e.g., target tissues in the brain) that is to be treated, via the cranial access device. The probe can be used to treat various brain diseases by using thermal ablation. The diseases can range from tumors to epilepsy. According to an embodiment, the probe is aligned to the target tissue and inserted into the brain until the tip reaches the target tissue. Thereafter, laser energy is transmitted through the probe and emitted from the tip inside the target area. The energy heats the tissues causing cell death. It must be appreciated that the temperature of the probe tip can be controlled using a cooling gas and thermal monitoring.

According to an embodiment, the skull mounted bolts or cranial access devices described above can be used in conjunction with a brain biopsy tool. The brain biopsy tool may be positioned and deployed within the target brain area via the cranial access device.

According to an embodiment, the skull mounted bolts or cranial access devices described above can be used in conjunction with a tools for placement of electrodes (e.g., Stereoelectroencephalography (SEEG)) within the brain. An electrode can be introduced and placed within a target area (e.g., target tissues in the brain), via the cranial access device.

By one embodiment, various agents may be introduced into the CNS of the subject, and in particular the brain of a subject, using the apparatus and methods of the present disclosure. A variety of agents and compositions comprising such agents can be delivered using the device, including but not limited to chemotherapeutic agents, agents for treatment of neurodegenerative disease (e.g., neurotrophic factors or neuroprotective agents), antiepileptic agents, antidepressant agents, antipsychotic agents, anti-inflammatory agents, antifibrotic agents, antianxiolytics and the like.

By one embodiment, the agents delivered using the methods and devices of the present disclosure include gene therapy by delivery of transgenes encoding certain factors into the brain, which offers great promise for treating neurodegenerative conditions such as Alzheimer's disease, Parkinson's disease and Huntington's disease. Similarly, cell-based therapies typically require quite precise placement of the cell population into the targeted region of the CNS. Delivery of these agents requires that the therapeutic composition dosage be consistently provided at precise locations in the brain to ensure that a predictable amount of the intended cell or encoded factor be delivered only to targeted regions of the brain. Such precise delivery requires delivery vectors and cells encoding transgenes to be grafted at pre-determined sites in the target brain region. The apparatus and delivery system of the present disclosure allow a precise and localized introduction of such agents into targeted regions of the brain while minimizing the invasiveness of the surgical procedure. Therefore, improvements in therapeutic efficacy can be obtained by enhancing the accurate placement of transgene-containing donor cell grafts and/or viral vectors into the brain using the apparatus and methods described herein.

Furthermore, agent delivery can be provided as a single dosage form, as a bolus or encapsulated dosage form which will release drug over time, and/or the implantation of delivery device (e.g., an osmotic pump or a catheter). Such devices for delivery of therapeutic agents that can be used in conjunction with the skull mounted bolts described herein.

As stated previously, the skull mounted bolt is robust, accurate, and provides a seamless way to provide stereotactic guidance, placement and fixation for the operation of instruments or devices. Additionally, the skull mounted bolt described herein has a slim profile, which provisions multiple bolts to be inserted into the skull within close proximity of one another.

It will be understood that terms such as "same," "equal," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to emphasize this meaning, unless the context or other statements clearly indicate otherwise. For example, items described as "substantially the same," "substantially equal," or "substantially planar," may be exactly the same, equal, or planar, or may be the same, equal, or planar within acceptable variations that may occur, for example, due to manufacturing processes and/or tolerances. The term "substantially" may be used to encompass this meaning, especially when such variations do not materially alter functionality.

It will be understood that various modifications may be made to the embodiments disclosed herein. Likewise, the above disclosed methods may be performed according to an alternate sequence. Therefore, the above description should not be construed as limiting, but merely as exemplification of the various embodiments. Those skilled in the art will envision other modifications within the scope and spirit of the claims appended hereto.

What is claimed is:

1. A cranial access device comprising:
    a cranial bolt comprising:
        a distal threaded portion,
        a proximal drive portion comprising a plurality of protrusions that form an external drive geometry, and
        a central passageway configured for receiving a neurosurgical tool; and
    a drive adapter comprising:
        a distal end configured to receive and interface with the external drive geometry of the proximal drive portion, and
        a proximal end configured to receive a driver tool, and
        wherein a first outer diameter of a section of the cranial bolt between the proximal drive portion and the distal threaded portion is substantially equal to or is less than an outer diameter of the drive adapter.

2. The cranial access device of claim 1, wherein the cranial bolt is manufactured using a non-conductive, rigid material that substantially reduces formation of artifacts during magnetic resonance imaging.

3. The cranial access device of claim 2, wherein the non-conductive rigid material is ceramic.

4. The cranial access device of claim 1, wherein the drive adapter is manufactured using a semi-rigid material.

5. The cranial access device of claim 1, wherein the distal threaded portion is configured for self-tapping of the cranial bolt into a skull hole.

6. The cranial access device of claim 5, wherein the distal threaded portion includes a distal end that does not include threads.

7. The cranial access device of claim 1, further comprising at least one reducing tube for modifying a diameter of the central passageway.

8. The cranial access device of claim 1, wherein the central passageway is further configured to receive at least a portion of a drive pin of the driver tool.

9. The cranial access device of claim 1, wherein a second outer diameter of a second section of the cranial bolt between the proximal drive portion and the distal threaded portion is less than the first outer diameter.

10. The cranial access device of claim 1, wherein a torque tolerance of the drive adapter is less than a torque tolerance of the cranial bolt.

11. A kit for use in neurosurgery comprising:
    a driver tool; and
    a cranial access device comprising:
        a cranial bolt comprising:
            a distal threaded portion,
            a proximal drive portion comprising a plurality of protrusions that form an external drive geometry, and
            a central passageway configured for receiving a neurosurgical tool; and
        a drive adapter comprising:
            a distal end configured to receive and interface with the external drive geometry of the proximal drive portion, and
            a proximal end configured to receive the driver tool,
        wherein the driver tool is inserted into the cranial access device to provide a continuous lumen for insertion into a stereotactic device during a surgical procedure; and
        wherein a first outer diameter of a section of the cranial bolt between the proximal drive portion and the distal threaded portion is substantially equal to or is less than an outer diameter of the drive adapter.

12. The kit of claim 11, wherein the cranial bolt is manufactured using a rigid material that substantially reduces formation of artifacts during magnetic resonance imaging.

13. The kit of claim 12, wherein the rigid material is ceramic.

14. The kit of claim 11, wherein the drive adapter is manufactured using a semi-rigid material.

15. The kit of claim 11, wherein the distal threaded portion is configured for self-tapping of the cranial bolt into a skull hole.

16. The kit of claim 15, wherein the distal threaded portion includes a distal end that does not include threads.

17. The kit of claim 11, further comprising at least one reducing tube for modifying a diameter of the central passageway of the cranial bolt.

18. The kit of claim 11, wherein the central passageway is further configured to receive at least a portion of a drive pin of the driver tool.

* * * * *